United States Patent
Lee et al.

(10) Patent No.: US 11,862,764 B2
(45) Date of Patent: Jan. 2, 2024

(54) NON-AQUEOUS ELECTROLYTE COMPRISING ADDITIVE FOR NON-AQUEOUS ELECTROLYTE, AND LITHIUM SECONDARY BATTERY COMPRISING THE SAME

(71) Applicant: LG Energy Solution, Ltd., Seoul (KR)

(72) Inventors: Jung Min Lee, Daejeon (KR); Kyung Mi Lee, Daejeon (KR); Chul Eun Yeom, Daejeon (KR); Jung Gu Han, Daejeon (KR); Chul Haeng Lee, Daejeon (KR)

(73) Assignee: LG Energy Solution, Ltd.

( * ) Notice: Subject to any disclaimer, the term of this patent is extended or adjusted under 35 U.S.C. 154(b) by 14 days.

(21) Appl. No.: 17/880,776

(22) Filed: Aug. 4, 2022

(65) Prior Publication Data
US 2023/0090340 A1    Mar. 23, 2023

(30) Foreign Application Priority Data

Aug. 6, 2021 (KR) .......... 10-2021-0103602
Jul. 28, 2022 (KR) .......... 10-2022-0093930

(51) Int. Cl.
| | | |
|---|---|---|
| H01M 10/0567 | (2010.01) | |
| C07D 311/16 | (2006.01) | |
| H01M 4/505 | (2010.01) | |
| H01M 4/525 | (2010.01) | |
| H01M 10/0525 | (2010.01) | |
| H01M 10/0568 | (2010.01) | |
| H01M 10/0569 | (2010.01) | |
| H01M 4/02 | (2006.01) | |

(52) U.S. Cl.
CPC ....... *H01M 10/0567* (2013.01); *C07D 311/16* (2013.01); *H01M 4/505* (2013.01); *H01M 4/525* (2013.01); *H01M 10/0525* (2013.01); *H01M 10/0568* (2013.01); *H01M 10/0569* (2013.01); *H01M 2004/028* (2013.01); *H01M 2300/0037* (2013.01)

(58) Field of Classification Search
CPC .. H01M 10/0567; H01M 4/505; H01M 4/525; H01M 10/0525; H01M 10/0568; H01M 10/0569; H01M 2004/028; H01M 2300/0037; H01M 2220/20; H01M 10/052; C07D 311/16; Y02E 60/10
See application file for complete search history.

(56) References Cited

U.S. PATENT DOCUMENTS

| | | |
|---|---|---|
| 2004/0185347 A1 | 9/2004 | Kim et al. |
| 2008/0138703 A1 | 6/2008 | Deguchi et al. |
| 2022/0209299 A1 | 6/2022 | Lee et al. |

FOREIGN PATENT DOCUMENTS

| | | | | |
|---|---|---|---|---|
| CN | 102569889 | * | 7/2012 | ........ H01M 10/0567 |
| CN | 102569889 A | | 7/2012 | |
| CN | 107699917 A | | 2/2018 | |
| JP | H10050344 A | | 2/1998 | |
| JP | 2001338763 A | | 12/2001 | |
| JP | 2005114891 A | | 4/2005 | |
| KR | 20040080775 A | | 9/2004 | |
| KR | 20070090034 A | | 9/2007 | |
| KR | 20150128564 A | | 11/2015 | |
| KR | 20210060330 A | | 5/2021 | |
| KR | 1020210060330 | * | 5/2021 | .......... H01M 10/052 |

* cited by examiner

Primary Examiner — Michael L Dignan
(74) Attorney, Agent, or Firm — Lerner David LLP

(57) ABSTRACT

The present disclosure provides a non-aqueous electrolyte including an additive for a non-aqueous electrolyte, which is represented by the following Chemical Formula 1:

[Chemical Formula 1]

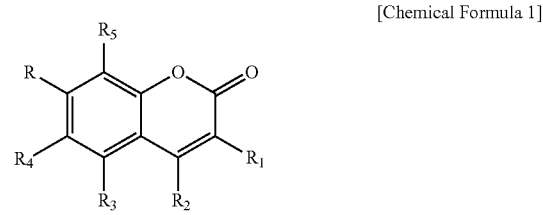

In Chemical Formula 1, $R_1$ to $R_5$ are each independently any one selected from the group consisting of H, an alkyl group having 1 to 10 carbon atoms, and an alkoxy group having 1 to 10 carbon atoms, and R may be an aliphatic unsaturated hydrocarbon group having 2 to 10 carbon atoms, or —OR' (R' is an aliphatic unsaturated hydrocarbon group having 2 to 10 carbon atoms).

12 Claims, No Drawings

NON-AQUEOUS ELECTROLYTE COMPRISING ADDITIVE FOR NON-AQUEOUS ELECTROLYTE, AND LITHIUM SECONDARY BATTERY COMPRISING THE SAME

CROSS-REFERENCE TO RELATED APPLICATION

This application claims priority from Korean Patent Application No. 10-2021-0103602 filed on Aug. 6, 2021, and Korean Patent Application No. 10-2022-0093930 filed on Jul. 28, 2022, the disclosures of which are incorporated herein by reference.

BACKGROUND OF THE INVENTION

The present disclosure relates to a non-aqueous electrolyte including an additive for a non-aqueous electrolyte, and a lithium secondary battery including the same.

Recently, as the application area of lithium secondary batteries has rapidly expanded not only to the power supply of electronic devices such as electrical devices, electronic devices, communication devices and computers, but also to the power storage supply of large area devices such as automobiles and power storage devices, there is an increasing demand for secondary batteries with high capacity, high output, and high stability.

In particular, high capacity, high output, and long service life characteristics have become important for lithium secondary batteries for automobile applications. In order to increase the capacity of a secondary battery, a high-nickel positive electrode active material having a high energy density but low stability may be used, or the secondary battery may be driven at a high voltage.

However, when the secondary battery is driven under the above conditions, a film or electrode surface structure formed on the surface of a positive/negative electrode is degraded by side reactions caused by the degradation of an electrolyte as the battery is charged and discharged, and transition metal ions may be eluted from the surface of the positive electrode. As described above, since the eluted transition metal ions degrade the passivation ability of SEI while being electro-deposited on the negative electrode, a problem in that the negative electrode is degraded occurs.

Such a degradation phenomenon of the secondary battery tends to be accelerated when the potential of the positive electrode increases or when the battery is exposed to high temperature.

Further, when a lithium-ion battery is used continuously for a long time or left to stand at high temperature, gas is generated, which causes a so-called swelling phenomenon in which the thickness of the battery is increased to occur, and in this case, it is known that the amount of gas varies depending on the state of such an SEI.

Therefore, in order to solve such a problem, research and development has been conducted for a method capable of reducing the swelling phenomenon of a secondary battery and enhancing stability at high temperature by suppressing the elution of metal ions from the positive electrode and forming a stable SEI film.

BRIEF SUMMARY OF THE INVENTION

As a result of conducting various studies to solve the above problems, the present disclosure is intended to provide an additive for a non-aqueous electrolyte, which is capable of suppressing the degradation of a positive electrode, reducing the side reaction between the positive electrode and an electrolyte, and forming a stable SEI film on a negative electrode.

In addition, the present disclosure is intended to provide a non-aqueous electrolyte whose stability at high temperature is enhanced by including the additive for a non-aqueous electrolyte.

Furthermore, the present disclosure is intended to provide a lithium secondary battery with improved overall performance by including the non-aqueous electrolyte to improve high temperature cycle characteristics and high temperature storage characteristics.

According to an exemplary embodiment, to achieve the objects, the present disclosure provides a non-aqueous electrolyte including an additive for a non-aqueous electrolyte, which is represented by the following Chemical Formula 1:

[Chemical Formula 1]

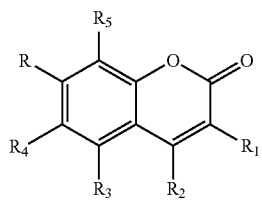

In Chemical Formula 1, $R_1$ to $R_5$ may each independently be any one selected from the group consisting of H, an alkyl group having 1 to 10 carbon atoms, and an alkoxy group having 1 to 10 carbon atoms, and R may be an aliphatic unsaturated hydrocarbon group having 2 to 10 carbon atoms, or —OR' (R' is an aliphatic unsaturated hydrocarbon group having 2 to 10 carbon atoms).

According to another exemplary embodiment, the present disclosure provides a lithium secondary battery including the non-aqueous electrolyte.

DETAILED DESCRIPTION OF THE INVENTION

Terms or words used in the specification and the claims should not be interpreted as being limited to typical or dictionary meanings and should be interpreted with a meaning and a concept that are consistent with the technical spirit of the present disclosure.

In the present disclosure, the term "comprise", "include", or "have" is intended to indicate the presence of the characteristic, number, step, constituent element, or any combination thereof implemented, and should be understood to mean that the possibility of the presence or addition of one or more other characteristics or numbers, steps, constituent elements, or any combination thereof is not precluded.

Further, in the description of "the carbon number a to b" in the present specification, "a" and "b" mean the number of carbon atoms included in a specific functional group. That is, the functional group may include "a" to "b" carbon atoms. For example, the "alkylene group having 1 to 5 carbon atoms" means an alkylene including carbon atoms with the number of carbon atoms 1 to 5, that is, —CH$_2$—, —CH$_2$CH$_2$—, —CH$_2$CH$_2$CH$_2$—, —CH$_2$(CH$_2$)$_3$CH$_2$—, —CH(CH$_3$)CH$_2$—, —CH(CH$_3$)CH$_2$CH$_2$—, and the like.

In addition, in the present specification, the alkyl group or the alkylene group may be substituted or unsubstituted on otherwise defined. The "substitution" means that at least one hydrogen bonded to carbon is substituted with an element other than hydrogen, and means being substituted with an alkyl group having 1 to 20 carbon atoms, an alkenyl group having 2 to 20 carbon atoms, an alkynyl group having 2 to 20 carbon atoms, an alkoxy group having 1 to 20 carbon atoms, a cycloalkyl group having 3 to 12 carbon atoms, a cycloalkenyl group having 3 to 12 carbon atoms, a heterocycloalkyl group having 3 to 12 carbon atoms, an aryloxy group having 6 to 12 carbon atoms, a halogen atom, a fluoroalkyl group having 1 to 20 carbon atoms, a nitro group, an aryl group having 6 to 20 carbon atoms, a heteroaryl group having 2 to 20 carbon atoms, a haloaryl group having 6 to 20 carbon atoms, and the like.

Hereinafter, the present disclosure will be described in more detail.

Non-Aqueous Electrolyte

A non-aqueous electrolyte according to an exemplary embodiment of the present disclosure includes a compound represented by the following Chemical Formula 1. A secondary battery including the non-aqueous electrolyte of the present disclosure may have excellent high temperature cycle characteristics and excellent high temperature storage characteristics because the degradation caused by an interfacial reaction at high temperature is suppressed.

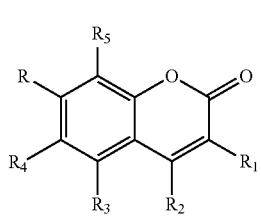

[Chemical Formula 1]

In Chemical Formula 1, $R_1$ to $R_5$ may each independently be any one selected from the group consisting of H, an alkyl group having 1 to 10 carbon atoms, and an alkoxy group having 1 to 10 carbon atoms, preferably any one selected from the group consisting of H, an alkyl group having 1 to 5 carbon atoms and an alkoxy group having 1 to 5 carbon atoms, and most preferably H.

In Chemical Formula 1, R may be an aliphatic unsaturated hydrocarbon group having 2 to 10 carbon atoms, or —OR' (R' is an aliphatic unsaturated hydrocarbon group having 2 to 10 carbon atoms). Preferably, R may be an aliphatic unsaturated hydrocarbon group having 2 to 5 carbon atoms, or —OR' (R' is an aliphatic unsaturated hydrocarbon group having 2 to 5 carbon atoms). By additionally including an aliphatic unsaturated hydrocarbon in the coumarin structure, a dense film may be formed on the electrode, whereby there is an effect of suppressing the degradation caused by an interfacial reaction at high temperature.

In Chemical Formula 1, the aliphatic unsaturated hydrocarbon group may include a triple bond. When R of Chemical Formula 1 includes a triple bond, a dense film may be formed on the electrode, whereby there is an effect of suppressing the degradation caused by an interfacial reaction at high temperature.

Further, in Chemical Formula 1, R may be an alkenyl group or alkynyl group having 2 to 5 carbon atoms.

Specifically, the compound represented by Chemical Formula 1 of the present disclosure may be a compound represented by the following Chemical Formula 1-1.

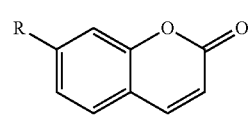

[Chemical Formula 1-1]

In Chemical Formula 1-1, R may be an aliphatic unsaturated hydrocarbon group having 2 to 10 carbon atoms, or —OR' (R' is an aliphatic unsaturated hydrocarbon group having 2 to 10 carbon atoms). Preferably, R may be an aliphatic unsaturated hydrocarbon group having 2 to 5 carbon atoms, or —OR' (R' is an aliphatic unsaturated hydrocarbon group having 2 to 5 carbon atoms). By additionally including an aliphatic unsaturated hydrocarbon in the coumarin structure, a dense film may be formed on the electrode, whereby there is an effect of suppressing the degradation caused by an interfacial reaction at high temperature.

In Chemical Formula 1-1, the aliphatic unsaturated hydrocarbon group may include a triple bond. When R of Chemical Formula 1-1 includes a triple bond, a dense film may be formed on the electrode, whereby there is an effect of suppressing the degradation caused by an interfacial reaction at high temperature.

In addition, in Chemical Formula 1-1, R may be an alkenyl group or alkynyl group having 2 to 5 carbon atoms.

Specifically, the compound represented by Chemical Formula 1 of the present disclosure may be any one of the compounds represented by the following Chemical Formulae 2-1 to 2-8.

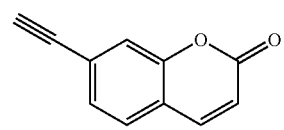

[Chemical Formula 2-1]

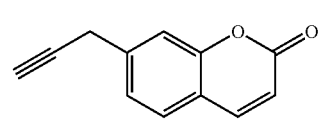

[Chemical Formula 2-2]

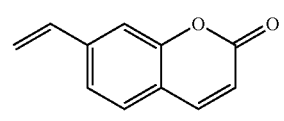

[Chemical Formula 2-3]

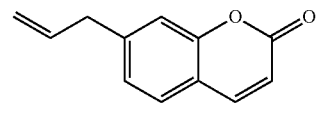

[Chemical Formula 2-4]

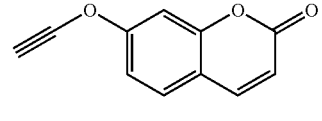

[Chemical Formula 2-5]

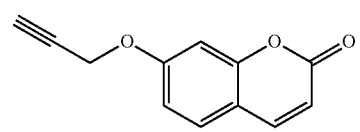

[Chemical Formula 2-6]

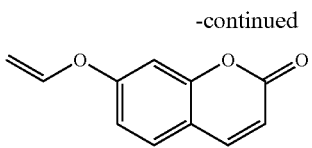
[Chemical Formula 2-7]

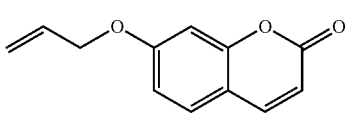
[Chemical Formula 2-8]

In the present disclosure, the additive for a non-aqueous electrolyte may be included in a content of 0.01 parts by weight to 5 parts by weight, preferably 0.1 parts by weight to 1 part by weight, and more preferably 0.1 parts by weight to 0.5 parts by weight, based on 100 parts by weight of the non-aqueous electrolyte. When the content of the compound represented by Chemical Formula 1 is less than the above range, the effect of suppressing degradation is not sufficiently exhibited, and when the content of the compound represented by Chemical Formula 1 exceeds the above range, a hydrocarbon group including an unsaturated bond increases the resistance of the secondary battery too much, and thus there is a problem in that life characteristics deteriorate.

When the content of the compound represented by Chemical Formula 1 is less than 0.01 parts by weight, an effect of forming the positive/negative electrode film becomes insignificant as the driving time increases, so the electrode interface protection effect may be reduced. Furthermore, when the content of the compound represented by Chemical Formula 1 exceeds 5 parts by weight, the viscosity of the electrolyte may be increased by an excessive amount of additive, and rate characteristics or life characteristics during storage at high temperature may deteriorate because the mobility of ions in the battery is adversely affected by a reduction in ion conductivity caused by an increase in viscosity. In addition, excessive decomposition of additives may increase battery resistance and cause side reactions and by-products.

The non-aqueous electrolyte according to the present disclosure may further include a lithium salt, an organic solvent and optionally other electrolyte additives.

The lithium salt is used as an electrolyte salt in a lithium secondary battery, and is used as a medium for transferring ions. Typically, the lithium salt includes, for example, $Li^+$ as a cation, and may include at least any one selected from the group consisting of $F^-$, $Cl^-$, $Br^-$, $I^-$, $NO_3^-$, $N(CN)_2^-$, $BF_4^-$, $ClO_4^-$, $B_{10}Cl_{10}^-$, $AlCl_4^-$, $AlO_2^-$, $PF_6^-$, $CF_3SO_3^-$, $CH_3CO_2^-$, $CF_3CO_2^-$, $AsF_6^-$, $SbF_6^-$, $CH_3SO_3^-$, $(CF_3CF_2SO_2)_2N^-$, $(CF_3SO_2)_2N^-$, $(FSO_2)_2N^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $C_4F_9SO_3^-$, $CF_3CF_2SO_3^-$, $CF_3CF_2(CF_3)_2CO^-$, $(CF_3SO_2)_2CH^-$, $CF_3(CF_2)_7SO_3^-$ and $SCN^-$.

Specifically, the lithium salt may include a single material or a mixture of two or more thereof selected from the group consisting of LiCl, LiBr, LiI, $LiBF_4$, $LiClO_4$, $LiB_{10}Cl_{10}$, $LiAlCl_4$, $LiAlO_2$, $LiPF_6$, $LiCF_3SO_3$, $LiCH_3CO_2$, $LiCF_3CO_2$, $LiAsF_6$, $LiSbF_6$, $LiCH_3SO_3$, $LiN(SO_2F)_2$ (lithium bis(fluorosulfonyl)imide; LiFSI), $LiN(SO_2CF_2CF_3)_2$ (lithium bis(perfluoroethanesulfonyl)imide; LiBETI) and $LIN(SO_2CF_3)_2$ (lithium bis(trifluoromethanesulfonyl)imide; LiTFSI). In addition to these, lithium salts typically used in an electrolyte for a lithium secondary battery may be used without limitation.

Although the lithium salt may be appropriately changed within a range that can be typically used, the lithium salt may be included at a concentration of 0.5 M to 5.0 M, preferably 0.8 M to 2.5 M, and more preferably 1.0 M to 2.0 M in order to obtain an optimum effect of forming a corrosion-preventing film on the electrode surface.

When the concentration of the lithium salt is less than 0.5 M, a condition under which lithium is excessively deficient is created, so the capacity and cycle characteristics may deteriorate, and when the concentration exceeds 5.0 M, electrolyte impregnability deteriorates as the viscosity of the non-aqueous electrolyte is increased excessively, and performance deterioration caused by an increase in battery resistance may occur.

The non-aqueous organic solvent may include at least one or more organic solvents selected from the group consisting of a cyclic carbonate-based organic solvent, a linear carbonate-based organic solvent, a linear ester-based organic solvent and a cyclic ester-based organic solvent.

Specifically, the organic solvent may include a cyclic carbonate-based organic solvent, a linear carbonate-based organic solvent or a mixed organic solvent thereof.

The cyclic carbonate-based organic solvent is a high-viscosity organic solvent that has a high dielectric constant, and thus can dissociate the lithium salt in the electrolyte well, and may include at least one or more organic solvents selected from the group consisting of ethylene carbonate (EC), propylene carbonate (PC), 1,2-butylene carbonate, 2,3-butylene carbonate, 1,2-pentylene carbonate, 2,3-pentylene carbonate and vinylene carbonate as specific examples thereof, and may include ethylene carbonate among them.

Further, the linear carbonate-based organic solvent is an organic solvent having low viscosity and a low dielectric constant, it is possible to use at least one or more organic solvents selected from the group consisting of dimethyl carbonate (DMC), diethyl carbonate (DEC), dipropyl carbonate, ethyl methyl carbonate (EMC), methyl propyl carbonate and ethyl propyl carbonate as representative examples thereof, and specifically, the linear carbonate-based organic solvent may include ethyl methyl carbonate (EMC).

In addition, the organic solvent may additionally include at least one or more ester-based organic solvents selected from the group consisting of a linear ester-based organic solvent and a cyclic ester-based organic solvent in at least one or more carbonate-based organic solvents selected from the group consisting of the cyclic carbonate-based organic solvent and the linear carbonate-based organic solvent in order to prepare an electrolyte having high ion conductivity.

Specific examples of the linear ester-based organic solvent include at least one or more organic solvents selected from the group consisting of methyl acetate, ethyl acetate, propyl acetate, methyl propionate, ethyl propionate, propyl propionate and butyl propionate.

Furthermore, examples of the cyclic ester-based organic solvent include γ-butyrolactone, γ-valerolactone, γ-caprolactone, σ-valerolactone and ε-caprolactone.

Meanwhile, as the organic solvent, an organic solvent typically used for a non-aqueous electrolyte may be added without limitation, if necessary. For example, the organic solvent may additionally include at least one or more organic solvents of an ether-based organic solvent, a glyme-based solvent and a nitrile-based organic solvent.

As the ether-based solvent, it is possible to use any one or a mixture of two or more thereof selected from the group consisting of dimethyl ether, diethyl ether, dipropyl ether, methylethyl ether, methylpropyl ether, ethylpropyl ether, 1,3-dioxolane (DOL) and 2,2-bis(trifluoromethyl)-1,3-dioxolane (TFDOL), but the ether-based solvent is not limited thereto.

The glyme-based solvent is a solvent that has a higher dielectric constant and lower surface tension, and is less reactive with a metal than the linear carbonate-based organic solvent, and may include at least one or more selected from the group consisting of dimethoxyethane (glyme, DME), diethoxyethane, diglyme, triglyme, and tetraglyme (TEGDME).

The nitrile-based solvent may be one or more selected from the group consisting of acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile, but is not limited thereto.

Further, the non-aqueous electrolyte of the present disclosure may additionally include known electrolyte additives in the non-aqueous electrolyte, if necessary, in order to prevent the induction of collapse of an electrode due to the decomposition of the non-aqueous electrolyte in a high voltage environment, or to further improve low-temperature high-rate discharge characteristics, high temperature stability, the prevention of overcharge, a battery expansion suppression effect at high temperature, and the like.

Representative examples of these other electrolyte additives may include at least one or more additives for forming an SEI film selected from the group consisting of cyclic carbonate-based compounds, halogen-substituted carbonate-based compounds, sultone-based compounds, sulfate-based compounds, phosphate-based compounds, borate-based compounds, nitrile-based compounds, benzene-based compounds, amine-based compounds, silane-based compounds and lithium salt-based compounds.

Examples of the cyclic carbonate-based compound include vinylene carbonate (VC) or vinylethylene carbonate.

Examples of the halogen-substituted carbonate-based compound include fluoroethylene carbonate (FEC).

Examples of the sultone-based compound include at least one or more compounds selected from the group consisting of 1,3-propane sultone (PS), 1,4-butane sultone, ethene sultone, 1,3-propene sultone (PRS), 1,4-butene sultone and 1-methyl-1,3-propene sultone.

Examples of the sulfate-based compound include ethylene sulfate (Esa), trimethylene sulfate (TMS), or methyl trimethylene sulfate (MTMS).

Examples of the phosphate-based compound include one or more compounds selected from lithium difluoro (bisoxalato)phosphate, lithium difluorophosphate, tetramethyl trimethyl silyl phosphate, trimethyl silyl phosphite, tris(2,2,2-trifluoroethyl)phosphate, or tris(trifluoroethyl)phosphite.

Examples of the borate-based compound include tetraphenylborate, lithium oxalyldifluoroborate (LiODFB), and lithium bisoxalatoborate (LiB($C_2O_4$)$_2$, LiBOB).

Examples of the nitrile-based compound include at least one or more compounds selected from the group consisting of succinonitrile, adiponitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

Examples of the benzene-based compound include fluorobenzene, examples of the amine-based include triethanolamine, ethylene diamine, or the like, and examples of the silane-based compound include tetravinylsilane.

The lithium salt-based compound is a compound different from the lithium salt included in the non-aqueous electrolyte, and examples thereof include lithium difluorophosphate (LiDFP), $LiPO_2F_2$, or the like.

When a combination of vinylene carbonate (VC), 1,3-propane sultone (PS), ethylene sulfate (Esa), and lithium difluorophosphate (LiDFP) is additionally included in these other electrolyte additives, during the initial activation process of the secondary battery, a more solid SEI film may be formed on the surface of the negative electrode, and the high temperature stability of the secondary battery may be improved by suppressing the generation of gas which may be produced by the decomposition of the electrolyte at high temperature.

Meanwhile, the other electrolyte additives may be used in mixtures of two or more thereof, and may be included in an amount of 0.01 to 20 wt %, specifically 0.01 to 10 wt %, and preferably 0.05 to 5 wt %, based on the total weight of the non-aqueous electrolyte. When the content of the other electrolyte additives is less than 0.01 wt %, the effect of improving the high temperature storage characteristics and high temperature life characteristics of the battery is insignificant, and when the content of the other electrolyte additives exceeds 20 wt %, side reactions in the electrolyte may occur excessively during charging and discharging of the battery. In particular, when the other electrolyte additives are added in an excessive amount, the additives are not sufficiently decomposed at high temperature, and thus may be present while being unreacted or precipitated in the electrolyte at room temperature. Accordingly, side reactions, in which the life or resistance characteristics of the secondary battery deteriorate, may occur.

Lithium Secondary Battery

The present disclosure also provides a lithium secondary battery including the non-aqueous electrolyte.

Specifically, the lithium secondary battery includes a positive electrode including a positive electrode active material, a negative electrode including a negative electrode active material, a separator interposed between the positive electrode and the negative electrode, and the above-described non-aqueous electrolyte.

In this case, the lithium secondary battery of the present disclosure may be manufactured by a typical method known in the art. For example, after a positive electrode, a negative electrode and a separator between the positive electrode and the negative electrode are sequentially stacked to form an electrode assembly, the lithium secondary battery may be manufactured by inserting the electrode assembly into a battery case and injecting the non-aqueous electrolyte according to the present disclosure into the resultant.

(1) Positive Electrode

The positive electrode may be manufactured by coating a positive electrode current collector with a positive electrode including a positive electrode active material, a binder, a conductive material, a solvent, and the like.

The positive electrode current collector is not particularly limited as long as the collector has conductivity without causing a chemical change to the battery, and for example, it is possible to use stainless steel; aluminum; nickel; titanium; calcined carbon, or aluminum or stainless steel surface-treated with carbon, nickel, titanium, silver, and the like.

The positive electrode active material is a compound enabling reversible intercalation and deintercalation of lithium, and specifically, the positive electrode active material may include a lithium metal oxide including lithium and one or more metals such as cobalt, manganese, nickel or aluminum. More specifically, examples of the lithium metal oxide include a lithium-manganese-based oxide (for example, $LiMnO_2$, $LiMn_2O_4$, and the like), a lithium-cobalt-based oxide (for example, $LiCoO_2$, and the like), a lithium-nickel-based oxide (for example, $LiNiO_2$, and the like), a lithium-nickel-manganese-based oxide (for example, $LiNi_{1-Y}Mn_YO_2$ (here, $0<Y<1$), $LiMn_{2-Z}Ni_ZO_4$ (here, $0<Z<2$), and the like), a lithium-nickel-cobalt-based oxide (for example, $LiNi_{1-Y1}Co_{Y1}O_2$ (here, $0<Y1<1$) and the like), a lithium-manganese-cobalt-based oxide (for example, $LiCo_{1-Y2}Mn_{Y2}O_2$ (here, $0<Y2<1$), $LiMn_{2-z1}Co_{z1}O_4$ (here, $0<Z1<2$), and the like), a lithium-nickel-manganese-cobalt-based oxide (for example, $Li(Ni_pCo_qMn_{r1})O_2$ (here, $0<p<1$, $0<q<1$, $0<r1<1$, $p+q+r1=1$) or $Li(Ni_{p1}Co_{q1}Mn_{r2})O_4$ (here, $0<p1<2$, $0<q1<2$, $0<r2<2$, $p1+q1+r2=2$), and the like), or a lithium-nickel-cobalt-transition metal (M) oxide (for example, $Li(Ni_{p2}Co_{q2}Mn_{r3}M_{S2})O_2$ (here, M is selected from the group consisting of Al, Fe, V, Cr, Ti, Ta, Mg, and Mo, p2, q2, r3, and s2 are each an atomic fraction of an independent element, and $0<p2<1$, $0<q2<1$, $0<r3<1$, $0<s2<1$, and $p2+q2+r3+s2=1$), and the like), and the like, and among them, any one or two or more compounds may be included.

Among them, in view of enhancing the capacity characteristics and stability of a battery, the lithium metal oxide may be $LiCoO_2$, $LiMnO_2$, $LiNiO_2$, a lithium nickel manganese cobalt oxide (for example, $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, $Li(Ni_{0.5}Mn_{0.1}Co_{0.1})O_2$, and the like), a lithium nickel cobalt aluminum oxide (for example, $Li(Ni_{0.5}Co_{0.15}Al_{0.05})O_2$, and the like), and the like, and in consideration of remarkable improvement effects caused by controlling the type and content ratio of constituent elements forming a lithium composite metal oxide, the lithium composite metal oxide may be $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, $Li(Ni_{0.5}Mn_{0.1}Co_{0.1})O_2$, and the like, and among them, any one or a mixture of two or more may be used.

Among them, a positive electrode active material having a nickel content of 80 atm % or more among a total transition metal content may be used in that the capacity characteristics of the battery may be most enhanced. For example, the positive electrode active material may include a lithium transition metal oxide represented by the following [Chemical Formula 3].

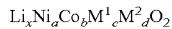

$$Li_xNi_aCo_bM^1_cM^2_dO_2 \quad \text{[Chemical Formula 3]}$$

In Chemical Formula 3, $M^1$ is one or more selected from Mn or Al, and may be preferably Mn or a combination of Mn and Al.

$M^2$ may be one or more selected from the group consisting of Zr, B, W, Mg, Ce, Hf, Ta, La, Ti, Sr, Ba, F, P and S.

x represents an atomic fraction of lithium in the lithium transition metal oxide, and may be $0.90 \leq x \leq 1.1$, preferably $0.95 \leq x \leq 1.08$, and more preferably $1.0 \leq x \leq 1.08$.

a represents an atomic fraction of nickel among the metal elements except for lithium in the lithium transition metal oxide, and may be $0.80 \leq a < 1.0$, preferably $0.80 \leq a \leq 0.95$, and more preferably $0.80 \leq a \leq 0.90$. When the nickel content satisfies the above range, high capacity characteristics may be implemented.

b represents an atomic fraction of cobalt among the metal elements except for lithium in the lithium transition metal oxide, and may be $0<b<0.2$, $0<b\leq 0.15$, or $0.01 \leq b \leq 0.10$.

c represents an atomic fraction of $M^1$ among the metal elements except for lithium in the lithium transition metal oxide, and may be $0<c<0.2$, $0<c\leq 0.15$, or $0.01 \leq c \leq 0.10$.

d represents an atomic fraction of $M^2$ among the metal elements except for lithium in the lithium transition metal oxide, and may be $0 \leq d \leq 0.1$, or $0 \leq d \leq 0.05$.

The positive electrode active material may be included in an amount of 60 to 99 wt %, preferably 70 to 99 wt %, and more preferably 80 to 98 wt %, based on the total weight of the solid content in the positive electrode mixture slurry.

The binder is a component that assists in the binding between the active material and the conductive material, and the like and the binding to the current collector.

Examples of such a binder include polyvinylidene fluoride, polyvinyl alcohol, carboxymethyl cellulose (CMC), starch, hydroxypropyl cellulose, regenerated cellulose, polyvinylpyrrolidone, polytetrafluoroethylene, polyethylene (PE), polypropylene, ethylene-propylene-diene, sulfonated ethylene-propylene-diene, styrene-butadiene rubber, fluororubber, various copolymers thereof, and the like.

Typically, the binder may be included in an amount of 1 to 20 wt %, preferably 1 to 15 wt %, and more preferably 1 to 10 wt %, based on the total weight of the solid content in the positive electrode mixture slurry.

The conductive material is a component for further improving the conductivity of the positive electrode active material.

Such a conductive material is not particularly limited as long as it has conductivity without causing a chemical change to the battery, and it is possible to use, for example, carbon powder such as carbon black, acetylene black, Ketjen black, channel black, furnace black, lamp black or thermal black; graphite powder such as natural graphite, artificial graphite, or graphite; conductive fibers such as carbon fibers, carbon nanotubes, or metal fibers; carbon fluoride powder; conductive powders such as aluminum powder and nickel powder; conductive whiskers such as zinc oxide and potassium titanate; conductive metal oxides such as titanium oxide; conductive materials such as polyphenylene derivatives, or the like.

Typically, the conductive material may be included in an amount of 1 to 20 wt %, preferably 1 to 15 wt %, and more preferably 1 to 10 wt %, based on the total weight of the solid content in the positive electrode mixture slurry.

The solvent may include an organic solvent such as N-methyl-2-pyrrolidone (NMP), and may be used in an amount to obtain a preferred viscosity when including the positive electrode active material, and selectively, a binder, a conductive material, and the like. For example, the solvent may be included such that the concentration of the solid content including the positive electrode active material, and optionally the binder and the conductive material is 50 to 95 wt %, preferably 70 to 90 wt %, and more preferably 70 to 90 wt %.

(2) Negative Electrode

The negative electrode may be manufactured, for example, by coating a negative electrode current collector with a negative electrode mixture slurry including a negative electrode active material, a binder, a conductive material, a solvent, and the like, or a graphite electrode made of carbon (C) or a metal itself may be used as a negative electrode.

For example, when a negative electrode is manufactured by coating the negative electrode current collector with a negative electrode mixture slurry, the negative electrode current collector generally has a thickness of 3 to 500 μm. The negative electrode current collector is not particularly limited as long as the negative electrode current collector has high conductivity without causing a chemical change to the battery, and for example, it is possible to use copper, stainless steel, aluminum, nickel, titanium, calcined carbon, copper or stainless steel surface-treated with carbon, nickel, titanium, silver, and the like, an aluminum-cadmium alloy, and the like. In addition, similar to the positive electrode collector, the adhesion of a negative electrode active material may also be increased by forming fine irregularities on a surface of the negative electrode collector and the collector may be used in various forms such as a film, a sheet, a foil, a net, a porous body, a foaming body, and a nonwoven body.

Furthermore, the negative electrode active material may include at least one or more selected from the group consisting of lithium metal, a carbon material capable of reversibly intercalating/deintercalating lithium ions, metals or alloys of these metals and lithium, metal composite oxides, a material capable of doping and dedoping lithium, and transition metal oxides.

As the carbon material capable of reversibly intercalating/deintercalating lithium ions, any carbon-based negative electrode active material generally used in lithium ion secondary batteries may be used without particular limitation, and as a representative example thereof, crystalline carbon, amorphous carbon or a combination thereof may be used. Examples of the crystalline carbon include graphite such as amorphous, plate, flake, spherical or fibrous natural graphite or artificial graphite, and examples of the amorphous carbon include soft carbon (low temperature calcined carbon), hard carbon, mesophase pitch carbide, calcined coke, and the like.

As the metals or alloys of these metals and lithium, a metal selected from the group consisting of Cu, Ni, Na, K, Rb, Cs, Fr, Be, Mg, Ca, Sr, Si, Sb, Pb, In, Zn, Ba, Ra, Ge, Al and Sn or an alloy of these metals and lithium may be used.

As the metal composite oxide, it is possible to use those selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $LixFe_2O_3$ ($0 \leq x \leq 1$), $Li_xWO_2$ ($0 \leq x \leq 1$) and $Sn_xMe_{1-x}Me'_yO_z$ (Me: Mn, Fe, Pb, Ge; Me': Al, B, P, Si, Group 1, Group 2 and Group 3 elements of the Periodic Table, and a halogen; $0 \leq x \leq 1$; $1 \leq y \leq 3$; and $1 \leq z \leq 8$).

Examples of the material capable of doping and dedoping lithium include Si, $SiO_x$ ($0 < x \leq 2$), a Si—Y alloy (Y is an element selected from the group consisting of alkali metals, alkaline earth metals, Group 13 elements, Group 14 elements, transition metals, rare earth elements and combinations thereof, and is not Si), Sn, SnO2, Sn—Y (Y is an element selected from the group consisting of alkali metals, alkaline earth metals, Group 13 elements, Group 14 elements, transition metals, rare earth elements and combinations thereof, and is not Sn) and the like, and at least one of them and $SiO_2$ may also be mixed and used. The element Y may be selected from the group consisting of Mg, Ca, Sr, Ba, Ra, Sc, Y, Ti, Zr, Hf, Rf, V, Nb, Ta, dubnium (Db), Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ge, P, As, Sb, Bi, S, Se, Te, Po and a combination thereof.

Examples of the transition metal oxide include a lithium-containing titanium composite oxide (LTO), vanadium oxide, lithium vanadium oxide, and the like.

The negative electrode active material may be included in an amount of 60 to 99 wt %, preferably 70 to 99 wt %, and more preferably 80 to 98 wt %, based on the total weight of the solid content in the negative electrode mixture slurry.

The binder is a component that assists in the binding among the active material, the active material, and the current collector. Examples of such a binder include polyvinylidene fluoride (PVDF), polyvinyl alcohol, carboxymethyl cellulose (CMC), starch, hydroxypropyl cellulose, regenerated cellulose, polyvinylpyrrolidone, polytetrafluoroethylene, polyethylene, polypropylene, an ethylene-propylene-diene monomer, a sulfonated ethylene-propylene-diene monomer, styrene-butadiene rubber, fluororubber, various copolymers thereof, and the like.

Typically, the binder may be included in an amount of 1 to 20 wt %, preferably 1 to 15 wt %, and more preferably 1 to 10 wt %, based on the total weight of the solid content in the negative electrode mixture slurry.

The conductive material is a component that further improves the conductivity of the negative electrode active material, and is not particularly limited as long as it has conductivity without causing a chemical change to the battery, and it is possible to use, for example, carbon powder such as carbon black, acetylene black, Ketjen black, channel black, furnace black, lamp black or thermal black; graphite powder such as natural graphite, artificial graphite, or graphite; conductive fibers such as carbon fibers, carbon nanotubes, or metal fibers; carbon fluoride powder; conductive powders such as aluminum powder and nickel powder; conductive whiskers such as zinc oxide and potassium titanate; conductive metal oxides such as titanium oxide; conductive materials such as polyphenylene derivatives, or the like.

The conductive material may be included in an amount of 1 to 20 wt %, preferably 1 to 15 wt %, and more preferably 1 to 10 wt %, based on the total weight of the solid content in the negative electrode mixture slurry.

The solvent may include water or an organic solvent such as N-methyl-2-pyrrolidone (NMP), and may be used in an amount to obtain a preferred viscosity when including the negative electrode active material, and selectively, a binder, a conductive material, and the like. For example, the solvent may be included such that the concentration of the solid content including the negative electrode active material and optionally the binder and the conductive material is 50 wt % to 95 wt %, preferably 70 wt % to 90 wt %.

When a metal itself is used as the negative electrode, the negative electrode may be manufactured by a method of physically bonding, rolling or depositing the metal on a metal thin film itself or the negative electrode current collector. As the deposition method, an electrical deposition method or chemical vapor deposition method for metal may be used.

For example, the metal bonded/rolled/deposited on the metal thin film itself or the negative electrode current collector may include one metal or an alloy of two metals selected from the group consisting of lithium (Li), nickel (Ni), tin (Sn), copper (Cu) and indium (In).

(3) Separator

Further, as a separator, a typical porous polymer film used as a separator in the related art, for example, a porous polymer film made of a polyolefin-based polymer such as an ethylene homopolymer, a propylene homopolymer, an ethylene/butene copolymer, an ethylene/hexene copolymer and an ethylene/methacrylate copolymer may be used either alone or a laminate thereof can be used, or a typical porous nonwoven fabric, for example, a nonwoven fabric made of high-melting point glass fiber, polyethylene terephthalate fiber, and the like may be used, but the separator is not limited thereto. Furthermore, a coated separator including a ceramic component or a polymeric material may be used to secure heat resistance or mechanical strength and may be optionally used in a single-layered or multi-layered structure.

The external shape of the lithium secondary battery of the present disclosure is not particularly limited, but may be a cylindrical type using a can, a prismatic type, a pouch type, or a coin type.

Hereinafter, the present disclosure will be described in more detail through specific Examples. However, the following Examples are merely examples for facilitating the understanding of the present disclosure, and do not limit the scope of the present disclosure. Of course, it will be apparent to those skilled in the art that various changes and modifications can be made within the scope and technical spirit of the present disclosure, and such changes and modifications also fall within the scope of the appended claims.

EXAMPLES

Example 1

(Preparation of Non-Aqueous Electrolyte)

A non-aqueous solvent was prepared by dissolving $LiPF_6$, vinylene carbonate (VC), 1,3-propane sultone (PS), ethylene sulfate (Esa) and lithium difluorophosphate (LiDFP) in an organic solvent (volume ratio of ethylene carbonate (EC): ethyl methyl carbonate (EMC)=3:7) such that $LiPF_6$, vinylene carbonate (VC), 1,3-propane sultone (PS), ethylene sulfate (Esa) and lithium difluorophosphate (LiDFP) were 1.0 M, 0.5 wt %, 0.5 wt %, 1.0 wt % and 0.8 wt %, respectively, and a non-aqueous electrolyte was prepared by putting 0.1 g of 7-ethynylcoumarin (compound of Chemical Formula 2-1) into 99.9 g of the non-aqueous solvent.

(Manufacture of Lithium Secondary Battery)

A positive electrode mixture slurry (75.5 wt % solid content) was prepared by adding a positive electrode active material ($LiNi_{0.85}Co_{0.05}Mn_{0.07}Al_{0.03}O_2$), a conductive material (carbon nanotubes) and a binder (polyvinylidene fluoride) at a weight ratio of 98.0:0.7:1.3 to N-methyl-2-pyrrolidone (NMP) which is a solvent. A positive electrode was manufactured by applying the positive electrode mixture slurry to one surface of a positive electrode current collector having a thickness of 12 m and drying and roll-pressing the resultant.

A negative electrode mixture slurry (50 wt % solid content) was prepared by adding a negative electrode active material (artificial graphite), a conductive material (carbon black) and a binder (styrene-butadiene rubber) at a weight ratio of 96.5:1.5:2.0 to distilled water which is a solvent. A negative electrode was manufactured by applying the negative electrode mixture slurry to one surface of a negative electrode current collector (Cu thin film) having a thickness of 8 m and drying and roll-pressing the resultant.

After a polyethylene porous film separator was interposed between the positive electrode and the negative electrode prepared above in a dry room, a secondary battery was manufactured by injecting the prepared non-aqueous electrolyte.

Example 2

A secondary battery was manufactured in the same manner as in Example 1, except that a non-aqueous electrolyte was prepared by putting 0.3 g of 7-ethynylcoumarin (compound of Chemical Formula 2-1) into 99.7 g of the non-aqueous solvent prepared in Example 1.

Example 3

A secondary battery was manufactured in the same manner as in Example 1, except that a non-aqueous electrolyte was prepared by putting 0.5 g of 7-ethynylcoumarin (compound of Chemical Formula 2-1) into 99.5 g of the non-aqueous solvent prepared in Example 1.

Example 4

A secondary battery was manufactured in the same manner as in Example 1, except that a non-aqueous electrolyte was prepared by putting 1.0 g of 7-ethynylcoumarin (compound of Chemical Formula 2-1) into 99.0 g of the non-aqueous solvent prepared in Example 1.

Example 5

A secondary battery was manufactured in the same manner as in Example 2, except that a non-aqueous electrolyte was prepared by putting 0.3 g of 7-(Propargyloxy)coumarin (compound of Chemical Formula 2-6) instead of 0.3 g of 7-ethynylcoumarin (compound of Chemical Formula 2-1) into 99.7 g of the non-aqueous solvent prepared in Example 2.

Comparative Example 1

A secondary battery was manufactured in the same manner as in Example 1, except that a non-aqueous electrolyte was prepared using 100 g of the non-aqueous solvent prepared in Example 1.

Experimental Example 1—Evaluation of High Temperature Cycle Characteristics

For each of the secondary batteries manufactured in Examples 1 to 5 and Comparative Example 1, cycle characteristics were evaluated.

Specifically, after 100 cycles of charging and discharging were performed by setting the charging and discharging of each of the batteries manufactured in Examples 1 to 5 and Comparative Example 1 to 4.2 V at a constant current of 0.33 C and to 3.0 V at a constant current of 0.33 C, respectively, at 45° C. as 1 cycle, a capacity retention rate compared to the initial capacity after 100 cycles was measured. The results are shown in the following Table 1.

TABLE 1

| | Capacity retention rate (%) |
|---|---|
| Example 1 | 94.2 |
| Example 2 | 93.8 |
| Example 3 | 93.1 |
| Example 4 | 89.7 |
| Example 5 | 95.3 |
| Comparative Example 1 | 87.8 |

As shown in Table 1, it could be confirmed that Examples 1 to 5 using the additive for a non-aqueous electrolyte of the present disclosure had excellent life characteristics due to a high capacity retention rate compared to Comparative Example 1 not using the additive.

Experimental Example 2—Evaluation of High Temperature Storage Characteristics For each of the secondary batteries manufactured in Examples 1 to 5 and Comparative Example 1, high temperature storage characteristics were evaluated.

Specifically, each of the secondary batteries in Examples 1 to 5 and Comparative Example 1 was fully charged to 4.2 V, and then stored at 60° C. for 8 weeks.

Before the secondary battery was stored, the thickness of the cell body portion of the fully charged secondary battery was measured using a flat plate measuring device and set as a thickness of the initial secondary battery.

After 8 weeks, a thickness increased during the storage period of 8 weeks was calculated by again measuring the thickness of the cell body portion for the stored secondary battery using a flat plate measuring device. A rate of increase in thickness after 8 weeks was derived by calculating a percentage ratio of increase in thickness to the initial thickness of the secondary battery. The results are shown in the following Table 2.

TABLE 2

|  | Rate of increase in thickness (%) |
|---|---|
| Example 1 | 25.0 |
| Example 2 | 22.1 |
| Example 3 | 19.6 |
| Example 4 | 17.3 |
| Example 5 | 25.2 |
| Comparative Example 1 | 32.7 |

As shown in Table 2, it could be confirmed that the secondary batteries of Examples 1 to 5 had a smaller rate of increase in thickness, and thus less gas generation at high temperature after 4 weeks than the secondary battery of Comparative Example 1.

The compound represented by Chemical Formula 1 provided as the additive for a non-aqueous electrolyte of the present disclosure is a compound based on a coumarin structure, and can form a stable solid electrolyte interphase (SEI) film on the surface of the negative electrode while being rapidly reduced and decomposed during charging and discharging. Therefore, the degradation of the negative electrode can be prevented by suppressing a reduction in the passivation ability of SEI at high temperature. Further, a reactive oxygen compound generated at a positive electrode including a high-nickel positive electrode active material and the coumarin structure contained in the compound represented by Chemical Formula 1 are bonded to each other to have an effect of suppressing the decomposition of the electrolyte and the generation of gas.

In addition, the compound represented by Chemical Formula 1 provided as the additive for a non-aqueous electrolyte of the present disclosure can form a dense film on the electrode by additionally including an aliphatic unsaturated hydrocarbon in the coumarin structure. This has an effect of suppressing the degradation caused by an interfacial reaction at high temperature.

Therefore, since an electrode-electrolyte interface, which is stable and has low resistance even at high temperature, is formed when the non-aqueous electrolyte of the present disclosure including the compound of Chemical Formula 1 is used, high temperature cycle characteristics and high temperature storage characteristics are improved, and thus a lithium secondary battery with improved overall performance can be implemented.

What is claimed is:

1. A non-aqueous electrolyte comprising an additive represented by Chemical Formula 1:

[Chemical Formula 1]

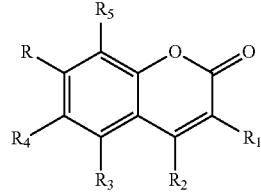

in Chemical Formula 1, $R_1$ to $R_5$ are each independently any one selected from the group consisting of H, an alkyl group having 1 to 10 carbon atoms, and an alkoxy group having 1 to 10 carbon atoms, and R is an aliphatic unsaturated hydrocarbon group having 2 to 10 carbon atoms, or —OR', wherein R' is an aliphatic unsaturated hydrocarbon group having 2 to 10 carbon atoms.

2. The non-aqueous electrolyte of claim 1, wherein R comprises a triple bond.

3. The non-aqueous electrolyte of claim 1, wherein R is an alkenyl group having 2 to 5 carbon atoms or an alkynyl group having 2 to 5 carbon atoms.

4. The non-aqueous electrolyte of claim 1, wherein the additive represented by Chemical Formula 1 is at least one or more selected from the group consisting of compounds represented by Chemical Formula 1-1:

[Chemical Formula 1-1]

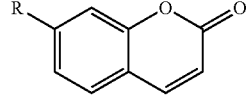

in Chemical Formula 1-1, R is an aliphatic unsaturated hydrocarbon group having 2 to 10 carbon atoms, or —OR', wherein R' is an aliphatic unsaturated hydrocarbon group having 2 to 10 carbon atoms.

5. The non-aqueous electrolyte of claim 1, wherein the additive represented by Chemical Formula 1 is at least one or more selected from the group consisting of compounds represented by Chemical Formula 2-1 to 2-8:

[Chemical Formula 2-1]

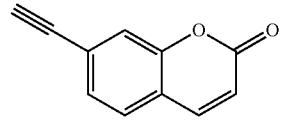

[Chemical Formula 2-2]

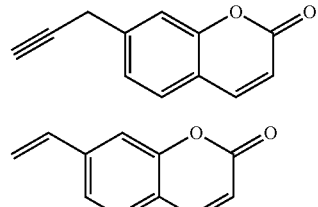

[Chemical Formula 2-3]

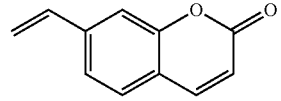

-continued

[Chemical Formula 2-4]
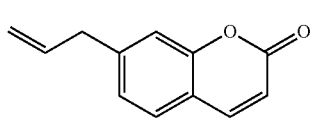

[Chemical Formula 2-5]
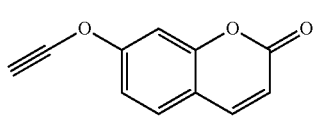

[Chemical Formula 2-6]
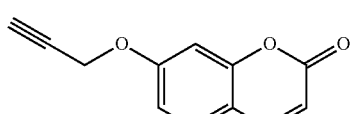

[Chemical Formula 2-7]
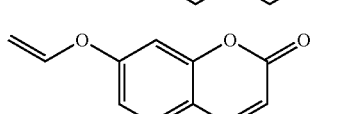

[Chemical Formula 2-8]
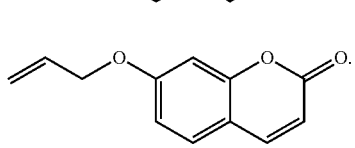

6. The non-aqueous electrolyte of claim 1, wherein the additive is comprised in an amount of 0.01 parts by weight to 5 parts by weight based on 100 parts by weight of the non-aqueous electrolyte.

7. The non-aqueous electrolyte of claim 1, further comprising a lithium salt and an organic solvent.

8. The non-aqueous electrolyte of claim 7, wherein the lithium salt is one or more selected from the group consisting of LiCl, LiBr, LiI, LiBF$_4$, LiClO$_4$, LiB$_{10}$Cl$_{10}$, LiAlCl$_4$, LiAlO$_2$, LiPF$_6$, LiCF$_3$SO$_3$, LiCH$_3$CO$_2$, LiCF$_3$CO$_2$, LiAsF$_6$, LiSbF$_6$, LiCH$_3$SO$_3$, LiN(SO$_2$F)$_2$, LiN(SO$_2$CF$_2$CF$_3$)$_2$ and LiN(SO$_2$CF$_3$)$_2$.

9. The non-aqueous electrolyte of claim 7, wherein the lithium salt is comprised at a concentration of 0.5 M to 5.0 M.

10. The non-aqueous electrolyte of claim 7, wherein the organic solvent comprises at least one or more organic solvents selected from the group consisting of a cyclic carbonate-based organic solvent, a linear carbonate-based organic solvent, a linear ester-based organic solvent and a cyclic ester-based organic solvent.

11. A lithium secondary battery comprising:
a positive electrode comprising a positive electrode active material;
a negative electrode comprising a negative electrode active material;
a separator interposed between the positive electrode and the negative electrode; and
the non-aqueous electrolyte of claim 1.

12. The lithium secondary battery of claim 11, wherein the positive electrode active material comprises a lithium transition metal oxide represented by Chemical Formula 3:

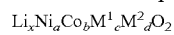   [Chemical Formula 3]

in Chemical Formula 3, M$^1$ is one or more selected from Mn or Al,
M$^2$ is one or more selected from the group consisting of Zr, B, W, Mg, Ce, Hf, Ta, La, Ti, Sr, Ba, F, P and S, and 0.90≤x≤1.1, 0.80≤a<1.0, 0<b<0.2, 0<c<0.2, 0≤d≤0.1.

* * * * *